(12) United States Patent
Bannister et al.

(10) Patent No.: US 11,510,728 B2
(45) Date of Patent: *Nov. 29, 2022

(54) MEDICAL IMAGING SYSTEM AND METHOD

(71) Applicant: Micrima Limited, Bristol (GB)

(72) Inventors: Peter Romilly Bannister, Bristol (GB); Andrew Farley, Bristol (GB)

(73) Assignee: Micrima Limited, Bristol (GB)

( * ) Notice: Subject to any disclaimer, the term of this patent is extended or adjusted under 35 U.S.C. 154(b) by 272 days.

This patent is subject to a terminal disclaimer.

(21) Appl. No.: 16/638,593

(22) PCT Filed: Aug. 16, 2018

(86) PCT No.: PCT/EP2018/072281
§ 371 (c)(1),
(2) Date: Feb. 12, 2020

(87) PCT Pub. No.: WO2019/034758
PCT Pub. Date: Feb. 21, 2019

(65) Prior Publication Data
US 2021/0161587 A1    Jun. 3, 2021

(30) Foreign Application Priority Data
Aug. 17, 2017  (EP) ..................... 17186740

(51) Int. Cl.
*A61B 18/18*   (2006.01)
*A61B 18/14*   (2006.01)
(Continued)

(52) U.S. Cl.
CPC ...... *A61B 18/1477* (2013.01); *A61B 18/1815* (2013.01); *A61B 5/002* (2013.01);
(Continued)

(58) Field of Classification Search
CPC ............ A61B 18/1477; A61B 18/1815; A61B 2018/00333; A61B 2018/00577;
(Continued)

(56) References Cited

U.S. PATENT DOCUMENTS 4,641,659 A * 2/1987 Sepponen ................. G01S 7/04
600/430
5,829,437 A * 11/1998 Bridges .................. A61B 6/502
600/407

(Continued)

FOREIGN PATENT DOCUMENTS

| JP | 2002-301074 A | 10/2002 |
| JP | 2007-512855 A | 5/2007 |
| WO | 2017021692 A1 | 2/2017 |

OTHER PUBLICATIONS

International Search Report for Application PCT/EP2018/072281 dated Dec. 17, 2018.
(Continued)

*Primary Examiner* — Michael F Peffley
(74) *Attorney, Agent, or Firm* — Honigman LLP

(57) ABSTRACT

A medical imaging system comprising: a microwave antenna array comprising a transmitting antenna and a plurality of receiving antennae, wherein the transmitting antenna is configured to transmit microwave signals so as to illuminate a body part of a patient and the receiving antennae are configured to receive the microwave signals following scattering within the body part; a processor configured to process the scattered microwave signals and generate an output indicative of the internal structure of the body part to identify a target within the body part; and an ablation probe comprising an ablation needle movable relative to the microwave antenna array; wherein the receiving antennae are further configured to receive microwave signals scattered or emitted by the ablation needle and the processor is further
(Continued)

configured to monitor a position of the ablation needle and to guide the ablation needle to the identified target within the body part which it can be used to perform an ablation procedure.

19 Claims, 7 Drawing Sheets

(51) Int. Cl.
  *A61B 5/00* (2006.01)
  *A61B 5/0507* (2021.01)
  *A61B 18/00* (2006.01)
(52) U.S. Cl.
  CPC ... *A61B 5/0507* (2013.01); *A61B 2018/00333* (2013.01); *A61B 2018/00577* (2013.01); *A61B 2018/00773* (2013.01); *A61B 2018/00791* (2013.01); *A61B 2018/1869* (2013.01)
(58) Field of Classification Search
  CPC .......... A61B 2018/00773; A61B 2018/00785; A61B 2018/00791; A61B 2018/00904; A61B 2018/1495; A61B 2018/1869; A61B 2034/2051; A61B 2090/397; A61B 34/20; A61B 34/30; A61B 5/002; A61B 5/0507; A61B 5/708; A61B 90/50
  See application file for complete search history.

(56) References Cited

U.S. PATENT DOCUMENTS

| | | | |
|---|---|---|---|
| 6,026,173 A | 2/2000 | Svenson et al. | |
| 6,546,279 B1* | 4/2003 | Bova | A61B 90/17 600/439 |
| 7,160,292 B2* | 1/2007 | Moorman | A61B 18/1815 606/41 |
| 7,266,407 B2* | 9/2007 | Li | A61B 5/0507 600/430 |
| 2004/0143150 A1* | 7/2004 | Barzell | A61N 5/1027 600/7 |
| 2004/0215101 A1* | 10/2004 | Rioux | A61B 90/11 600/562 |
| 2005/0149009 A1* | 7/2005 | Wakikaido | A61B 18/1815 607/156 |
| 2007/0197891 A1 | 8/2007 | Shachar et al. | |
| 2008/0027313 A1 | 1/2008 | Shachar | |
| 2011/0261180 A1* | 10/2011 | Simon | A61B 34/20 348/E7.085 |
| 2013/0303895 A1* | 11/2013 | Littrup | A61B 8/0825 600/424 |
| 2016/0022309 A1* | 1/2016 | Allaway | A61B 8/12 600/464 |
| 2016/0051221 A1 | 2/2016 | Dickhans et al. | |
| 2016/0106334 A1* | 4/2016 | Canli | A61B 5/7264 600/425 |

OTHER PUBLICATIONS

European Search Report for Application 20184609.4 dated Sep. 11, 2020.

Japanese Office Action, Application No. 2020-508050, dated Sep. 6, 2022.

\* cited by examiner

MEDICAL IMAGING SYSTEM AND METHOD

CROSS-REFERENCE TO RELATED APPLICATIONS

This U.S. patent application is a national phase application of International Application No. PCT/EP2018/072281, filed on Aug. 16, 2018, which claims priority to earlier-filed European Patent Application No. 17186740.1, filed on Aug. 17, 2017. The disclosures of these prior applications are considered part of the disclosure of this application and are hereby incorporated by reference in their entireties.

TECHNICAL FIELD

The invention relates to a medical imaging system and method and particularly, although not exclusively, to an apparatus and method which incorporates guidance of an ablation probe to a target.

BACKGROUND

Various medical imaging techniques are known for examining the human body. Such imaging techniques may be used to interrogate tissues and organs in order to identify abnormalities, such as tumors or lesions. For example, X-ray (mammography), microwave imaging, ultrasound, MRI are all common imaging modalities. Such techniques are commonly used to examine breast tissue, but may also be used in other areas of the body, such as the liver, pancreas, prostate, thyroid, lungs, ovaries and lymph nodes.

Once identified, a target, such as a tumor, can be treated using a suitable procedure. Typically, surgical resection has been the standard treatment of primary solid tumors localized to organs such as the lung, colon, and breast. However, needle ablation techniques such as radiofrequency ablation (RFA) and microwave ablation (MWA) provide a minimally invasive, nonsurgical alternative.

RFA uses a needle electrode to deliver radiofrequency current to the target which causes localized heating sufficient to achieve necrosis of malignant tissue, with only minimal destruction of the surrounding healthy cells.

RFA relies on electrical conduction through the tissue: RF current is able to pass through tissue because of the abundance of ionic fluid present. However, tissue is not a perfect conductor and RF current causes resistive heating (the Joule effect). Direct RF heating occurs within a few millimeters of the applicator (electrode), but a large portion of the final ablation zone is created when thermal conduction pushes heat into more peripheral areas around the electrode.

MWA uses a needle antenna or antennae to deliver microwave electromagnetic (EM) energy to the target.

MWA occurs as a result of dielectric heating of tissue. Dielectric heating occurs when an alternating EM field is applied to an imperfect dielectric material. In tissue, heating occurs because the EM field forces water molecules in the tissue to oscillate. The bound water molecules tend to oscillate out of phase with the applied fields, so some of the EM energy is absorbed and converted to heat. The best EM absorbers contain a high percentage of water (e.g., most solid organs) while less heating occurs in tissues with low water content (e.g., fat).

The invention seeks to provide a system which improves the treatment of a target within a body part.

SUMMARY

In accordance with an aspect of the invention, there is provided a medical imaging system comprising: a microwave antenna array comprising a transmitting antenna and a plurality of receiving antennae, wherein the transmitting antenna is configured to transmit microwave signals so as to illuminate a body part of a patient and the receiving antennae are configured to receive the microwave signals following scattering within the body part; a processor configured to process the scattered microwave signals and generate an output indicative of the internal structure of the body part to identify a target within the body part; and an ablation probe comprising an ablation needle movable relative to the microwave antenna array. The receiving antennae are further configured to receive microwave signals scattered or emitted by the ablation needle and the processor is further configured to monitor a position of the ablation needle as it is guided to the target within the body part.

The processor may be further configured to guide the ablation needle to the target within the body part.

The microwave antenna array may be formed on a substrate which may comprise one or more openings configured to receive the ablation needle to provide access to the body part.

The openings may be conical.

The openings may be provided with sealing gaskets.

The openings may comprise one or more slots.

The substrate may comprise a plurality of said openings and the processor may be configured to select one of the plurality of openings for introducing the ablation needle.

The ablation probe may be mounted on an articulated arm configured to maneuver the ablation probe relative to the antenna array.

The articulated arm may be a robotic arm.

The ablation needle may be configured to emit microwave signals which are received by the receiving antennae.

The ablation needle may comprise a coaxial feed line which transmits the microwave signals.

The ablation needle may comprise a microwave marker at its tip.

The processor may be configured to perform a first data acquisition and analysis operation when identifying the target and to perform a second data acquisition and analysis operation when guiding the ablation needle, the second data acquisition and analysis operation being faster than the first data acquisition and analysis operation.

The processor may be further configured to monitor the target during an ablation procedure performed by the ablation probe.

The receiving antennae of the microwave antenna array may receive a signal emitted by the ablation needle.

The processor may be further configured to determine a temperature or temperature profile of the target based on permittivity and/or conductivity values measured from the scattered microwave signals during an ablation procedure.

In accordance with another aspect of the invention there is provided a medical imaging method comprising: illuminating a body part of a patient with microwave signals emitted by a transmitting antenna of an microwave antenna array; receiving the microwave signals following scattering within the body part at a plurality of receiving antennae of the microwave antenna array; processing the scattered microwave signals to generate an output indicative of the internal structure of the body part; identifying a target within the body part from the output; guiding an ablation needle of an ablation probe to the target within the body part by monitoring microwave signals scattered or emitted by the ablation needle using the receiving antennae; and performing an ablation procedure using the ablation probe in which a signal is emitted from the ablation needle so as to heat the target.

The method may further comprise: monitoring the target during the ablation procedure.

Monitoring the target may comprise receiving at the receiving antennae of the microwave antenna array a signal emitted by the ablation needle during the ablation procedure.

Monitoring the target may comprise determining permittivity and/or conductivity values for the target from the scattered microwave signals received during the ablation procedure; and determining a temperature or temperature profile of the target based on the measured permittivity and/or conductivity.

BRIEF DESCRIPTION OF THE DRAWINGS

For a better understanding of the invention, and to show more clearly how it may be carried into effect, reference will now be made, by way of example, to the accompanying drawings, in which.

DETAILED DESCRIPTION

Figure 1:
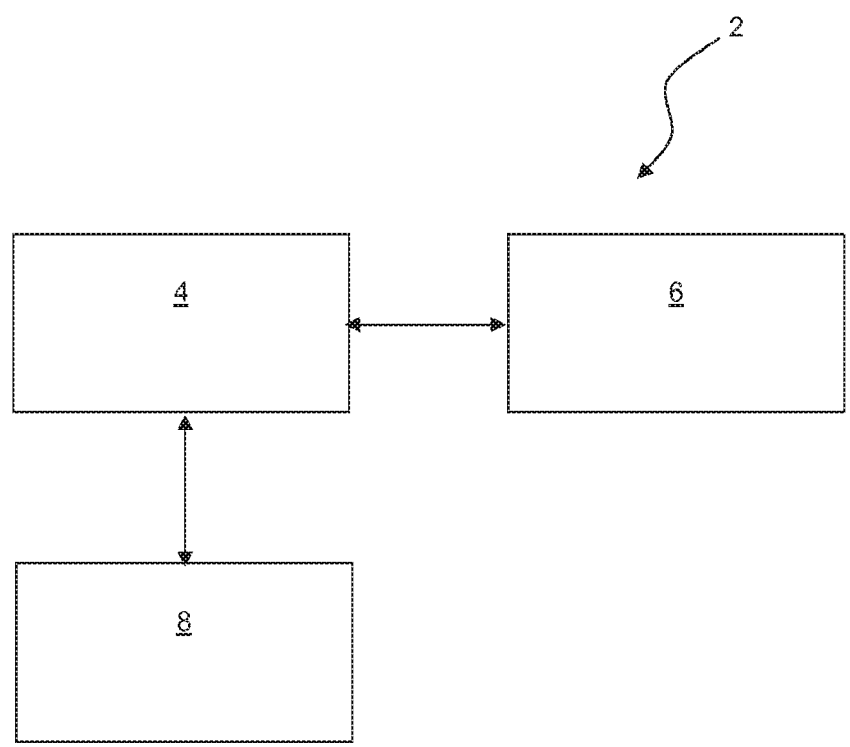
FIG. 1 is a system diagram of a medical imaging system according to an embodiment of the invention.

FIG. 1 shows a medical imaging system 2 according to an embodiment of the invention. The medical imaging system generally comprises a processor 4, a microwave antenna array 6 in communication with the processor 4, and an ablation system 8 in communication with the processor 4.

Figure 2:
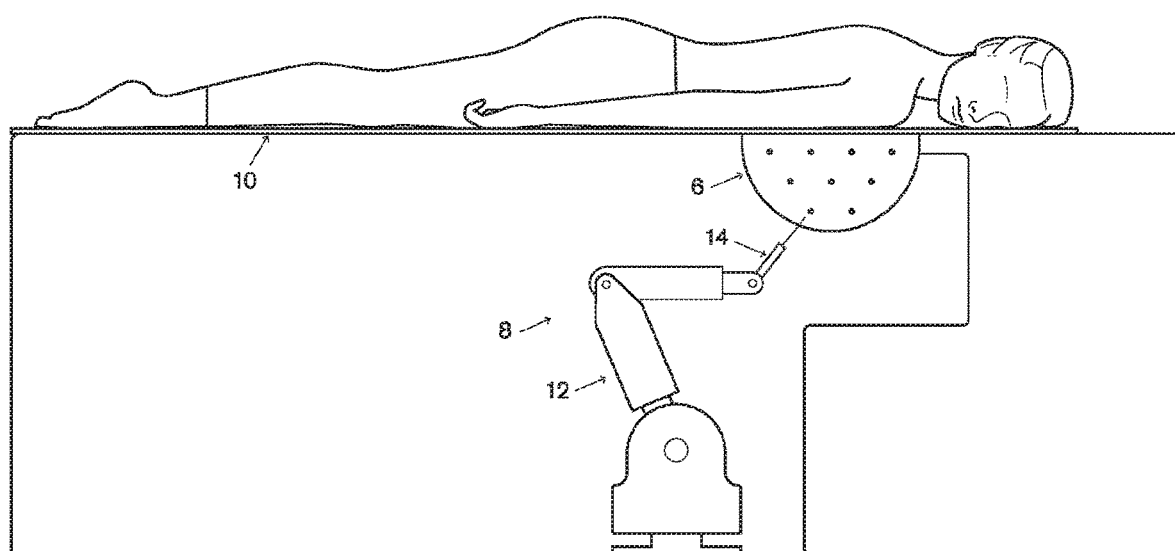
FIG. 2 is a schematic side view of an example implementation of the medical imaging system.

As shown in FIG. 2, the microwave antenna array 6 may form part of a table 10 on which a patient lies in a prone position. The ablation system 8 is connected to the table 10 or otherwise located in a fixed or known position relative to the table 10. The ablation system 8 comprises an articulated arm 12 which carries an ablation needle 14 (which may comprise one or more individual needles). The articulated arm 12 allows the ablation needle 14 to be maneuvered relative to the antenna array 6.

The ablation system 8 may be a radiofrequency ablation (RFA) system which uses a needle electrode or a microwave ablation (MWA) system which uses a needle antenna.

Figure 3:
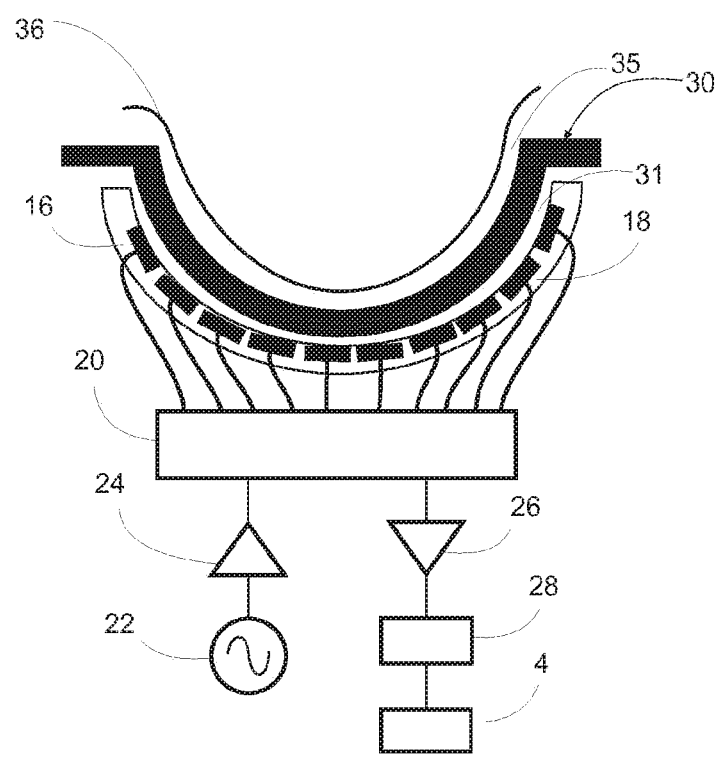
FIG. 3 is a schematic view of imaging portion of the medical imaging system.

As shown in FIG. 3, the antenna array 6 comprises a plurality N of antennae 16 which are arranged over the surface of, or within, a shell substrate 18. The shell 18 has a curved profile as shown. In particular, the shell 18 is part or hemi-spherical and is configured to approximate the shape of a breast. The antennae 16 are arranged over the shell 18 such that they all point to a common focal point.

The antennae 16 are each electrically connected to a switching matrix 20. The switching matrix 20 is in turn connected to both a transmit path and a receive path. The transmit path comprises a signal generator 22 coupled to an amplifier 24. The receive path comprises an amplifier 26 coupled to a detector 28 and the processor 4.

The switching matrix 20 selectively couples each of the antennae 16 to either the transmit path or the receive path.

The antenna array 6 is operated in a multi-static fashion. Specifically, the switching matrix 20 is controlled so as to connect one of the antennae 16 to the transmit path and the remaining antennae 16 to the receive path. The signal generator 22 generates a stepped frequency continuous wave (CW) signal which is amplified by the amplifier 24 and then transmitted by the antenna 16 connected to the transmit path. The stepped frequency continuous wave signal is a sequential series of pulses of continuous wave energy, where each pulse has its frequency stepped up across a range of frequencies, typically within the 3-8 GHz range. The other antennae 16 receive the transmitted signal and the received signal is detected and then recorded by the processor 4.

Figure 4:
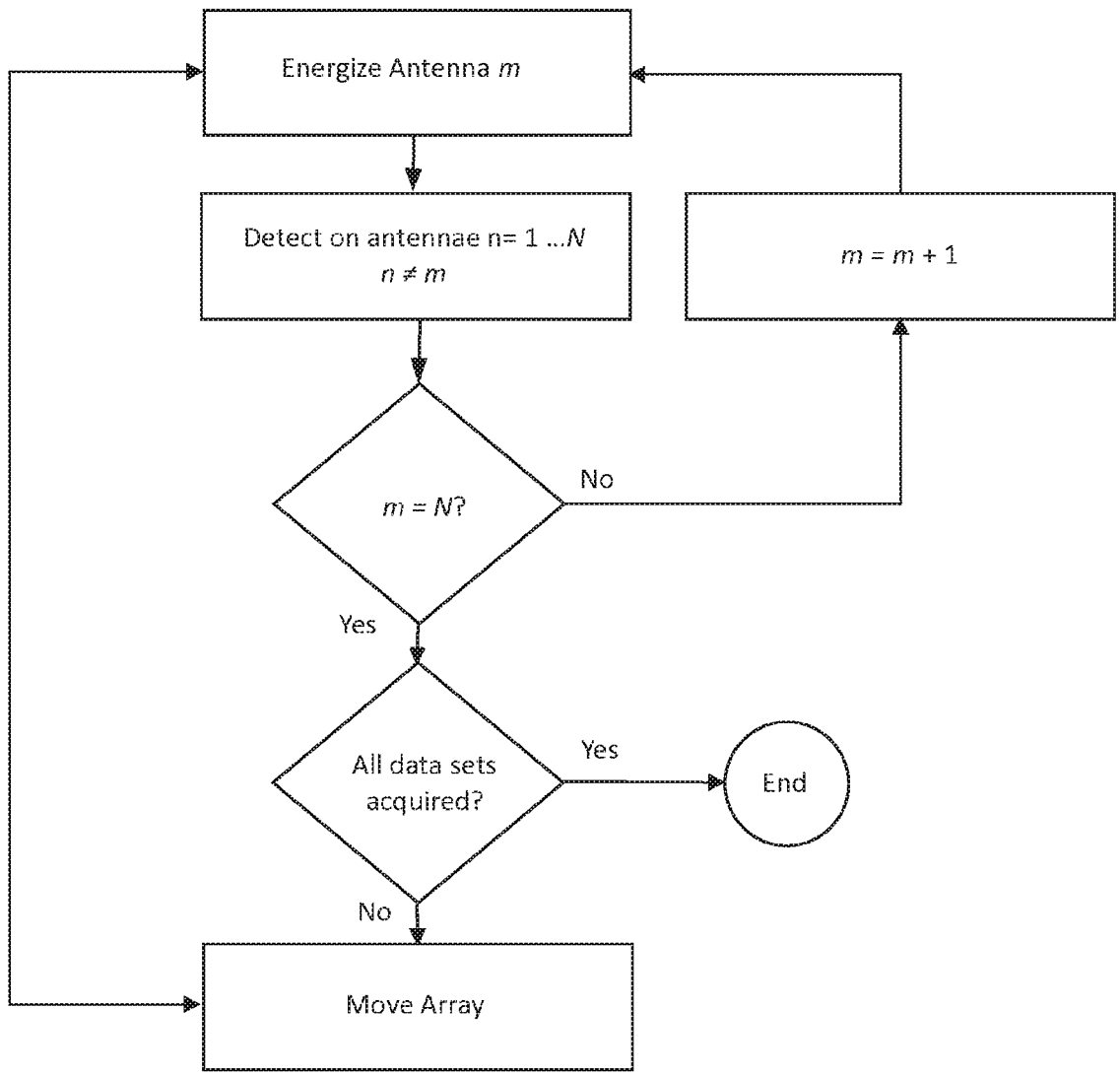
FIG. 4 is a flowchart depicting a sampling method.

FIG. 4 shows a flowchart of a data acquisition method. As shown, the switching matrix 20 connects an antenna m of the N antennae to the transmit path. All other antennae 16 (n=1 . . . N, n≠m) are connected to the receive path and detect the transmitted signal (possibly in a time-sharing arrangement). If m≠N, the switching matrix 20 steps to the next antenna 16 (m=m+1) to be connected to the transmit path. This is repeated until all antennae 16 have been connected to the transmit path. The acquisition process may be repeated with the antenna array 6 translated (i.e. rotated about its rotational axis). This may allow fixed errors to be cancelled from the detected signals.

Referring again to FIG. 3, the shell 18 receives a cup 30. The cup 30 has a complementary shape to the shell 18 such that if fits snugly within the shell 18.

The outside of the cup 30 and the inside of the shell 18 may have threaded portions to enable a threaded engagement between the cup 30 and the shell 18. The threaded engagement between the cup 30 and the shell 18 may be used to translate the antenna array 6 relative to the breast 36, as described previously.

A layer of coupling fluid (dielectric constant controlled fluid) may be inserted in the gap 31 between the shell 18 and the cup 30 so as to improve the coupling between the antennae 16 and the cup 30 in order to minimize signal loss and thus improve transmission of the microwave signal.

Figure 5:
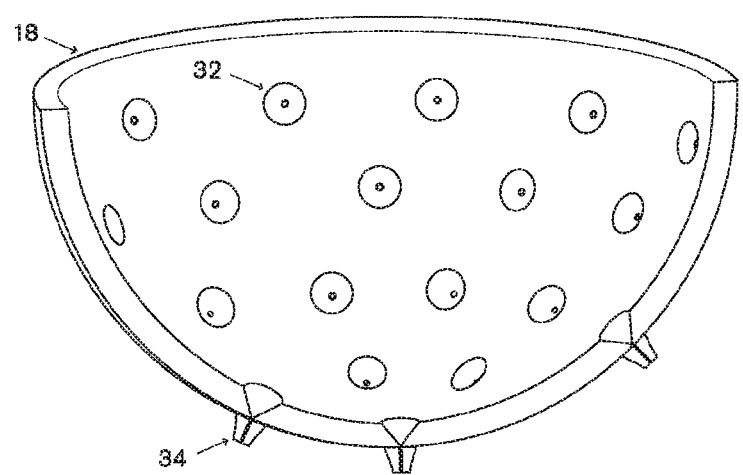
FIG. 5 is perspective cross-sectional view of an antenna shell of the medical imaging system.

As shown in FIG. 5, the shell 18 comprises a plurality of apertures 32 which are distributed across the surface of shell 18. Each aperture 32 extends through the thickness of the shell 18 and tapers such that the aperture 32 is wider at the inner surface of the shell 18 than at the outer surface. The apertures 32 are therefore frustoconical. Each aperture 32 is provided with a sealing nozzle or gasket 34. The gaskets 34 are provided in order to prevent the coupling fluid from leaking through the apertures 32. The cup 30 also comprises a set of corresponding apertures in order to provide access from the exterior of the shell 18 through to the interior of the cup 30.

In use, a patient lies on the table 10 in a prone position such that their breast 36 sits in the cup 30. A layer of coupling fluid may also be provided in the gap 35 between the cup 30 and the breast 36 in order to improve coupling between the antennae 16 and the breast 36.

Although not shown, one or more inserts may be placed inside the cup 30 so as to enable a better fit between the internal surface of the cup 30 and the breast 36. For example, a plurality of such inserts may be provided, each having different shapes and sizes, to enable the system to be better adapted to breasts of different shapes and sizes. The inserts may be made from the same material as the cup (e.g. ceramic).

The antenna 16 connected to the transmit path illuminates the breast 36 with the microwave signal. The signal is scattered by the breast tissue and the scattered signal is received at each of the non-transmitting antennae 16 where it is detected and recorded. This process is repeated for each antenna 16, as described previously with reference to the data acquisition method shown in FIG. 4.

The processor 4 may record the relative difference between the measured phase and amplitude of the transmitted signal as compared to the phase and amplitude of the scattered signal, recorded as a complex number (having real and imaginary parts).

The signal detected at each antenna 16 will generally comprise three components: a component arising from mutual coupling between the transmitting and receiving antennas 16; a component arising from radiation which reflects off the skin of the breast 36; and a component arising from radiation which reflects off structures within the breast (such as tumors). Tumors can generate identifiable reflections as they exhibit much higher dielectric properties than adipose tissues due to their significant water content. The mutual and skin reflection components may be removed or at least mitigated from the data set in order to improve the detectability of reflections resulting from the presence of tumors within the breast.

The acquired data set may be used by the processor 4 to construct an image of the internal structure of the breast 36. Data reconstruction may be performed using Phased Array (frequency domain), Delay and Sum (DAS—time domain) techniques or any other suitable technique. From this, the processor 4 is able to identify (possibly, with additional user input or confirmation) a region of interest (if present) in which a possible tumor or other pathology may exist. The presence of a tumor or other pathology may be confirmed by taking a biopsy from the region of interest.

Once the processor 4 (and any subsequent biopsy or other analysis) has identified a target, the ablation system 8 may be used to treat the target. In particular, the processor 4 may guide the articulated arm 12 so as to locate the ablation needle 14 in the desired position and orientation for accessing the target. The articulated arm 12 may be a robotic arm such that it can manipulate the ablation needle 14 to the required position and orientation based on coordinates provided by the processor 4. Alternatively, the articulated arm 12 may be actuated by a user but provide feedback via appropriate sensors to the user or processor 4 of its current position so that it can be brought into the proper position and orientation. As a further alternative, the articulated arm 12 may be dispensed with and the ablation needle 14 itself provide feedback via sensors on its current position and orientation to the processor 4 or user.

As described previously, the shell 18 comprises a plurality of apertures 32 which provide access to the breast 36 for the ablation needle 14.

The processor 4 may determine the most appropriate aperture 32 for performing the ablation procedure. In particular, the processor 4 may determine the closest aperture 32 to the target. As described previously, the apertures 32 are frustoconical such that the ablation needle 14 can be introduced through the aperture 32 at a range of angles.

With the ablation needle 14 guided to the appropriate position and orientation for accessing the target, the ablation needle 14 can be inserted into the breast 36 and directed to the target. The antenna array 6 can be used to confirm that the needle is coincident with the target by again illuminating the breast 36 with microwave signals and detecting scattered signals from the ablation needle 14. Specifically, the processor 4 may confirm that the ablation needle 14 is appropriately positioned prior to activation by updating the image. The image of the breast 36 (or only the relevant portion) may be updated as the ablation needle 14 passes into the breast 36 towards and into the target.

During the guidance of the ablation needle 14, the processor 4 may adjust the signal processing performed such that it is optimized for speed and mapping a known object in space. The data acquisition and analysis performed by the processor during the guidance of the ablation needle 14 may be faster than during imaging for the purpose of initially identifying the region of interest.

With the ablation needle 14 positioned at or within the target region, the ablation system 8 is activated so as to perform the ablation procedure (via a suitable signal generator and other electronics) in accordance with known practices and systems in order to heat the target so as to denature or kill cancerous cells. The parameters of the ablation procedure are controlled to ensure that the heating is localized to the target. If additional targets are present then the ablation needle 14 may again be guided to the next target either directly or following withdrawal of the ablation needle 14 from the breast.

The processor 4 and microwave antenna array 6 may be used to monitor the ablation procedure as it is being performed and to provide feedback to the clinician. In particular, the effect on the target may be measured directly by imaging the breast at a different frequency from the frequency of the ablation signal.

Alternatively or in addition, where the ablation system 8 is a MWA system, the microwave antenna array 6 may detect the microwave radiation from the needle itself which is spatially resolved. The processor 4 can therefore provide feedback on the propagation of the microwave radiation within the target and beyond. The parameters can therefore be controlled to ensure that the entire target (and no more) is ablated. The microwave radiation also gives information about the impedance match between the needle antenna and the surrounding tissue, allowing the needle antenna impedance to be better adjusted to optimize coupling of energy from the antenna to the surrounding tissue.

The target may continue to be imaged after the ablation procedure has been completed (e.g. immediately after or after a period of several days or weeks) so that the efficacy of the procedure can be understood. Such monitoring may be used to plan further treatment, such as further ablation procedures.

The data provided by the processor 4 and the microwave antenna array 6 provides a measure of the local conductivity and/or permittivity of the tissue being imaged. It has been found that conductivity and permittivity vary with temperature. Monitoring of the conductivity and/or permittivity of the target during the ablation procedure therefore provides information regarding the temperature of the target (or the surrounding tissue). A temperature profile of the target or a single average temperature for the entire region may be obtained from the data. The parameters (including the duration of the procedure) can be accurately controlled based on this temperature information to ensure that the tissue within the target reaches the required ablation temperature, but does not significantly exceed this in order to avoid propagation to surrounding tissue.

Ablation needles are typically made of steel which generally provides a strong microwave scattering signal and can therefore be reliably located. However, the ablation needle 14 may bend as it passes through tissue, and/or the scattering signal may be modified by surrounding tissue. To allow for either of these more complex cases, the ablation needle 14 may be modified so that it is more easily identifiable. In particular, the ablation needle 14 may be provided with a marker which is more easily discriminated by microwave radar in order to determine needle tip location and overall orientation more accurately.

Microwave markers will typically have one or more of the following characteristics:
   Enhanced overall microwave scattering amplitude over surrounding tissue
   Microwave scattering that is a strong function of frequency—the continuous wave radar is well suited to measure scattering as a function of frequency
   Scattering anisotropy—the hemispherical antenna array 6 is able to characterize scattering over a wide solid angle.

The marker should have a distinctive radar signature that can be characterized rapidly for guidance purposes. For example, the marker may include:
   Radio frequency identification tags
   Microwave metamaterials
   Ferromagnetically or ferrimagnetically resonant materials within the UWB band, such as ferrites.

The ablation needle 14 may be able to deposit such a marker at the site of the target in order to allow the site to be identified more easily in subsequent procedures, such as further ablation treatment or surgery.

Alternatively, the ablation needle 14 itself may radiate the microwave signal, rather than scattering signals generated by the antennae 16. For example, the ablation needle 14 may have an integrated coaxial feed line which supplies the signal to the tip of the needle. Where the ablation system 8 is a MWA system, the ablation needle 14 may radiate the microwave signal at the same frequency as that of microwave ablation or at another frequency. In this case, the needle antenna 14 may have an integrated coaxial feed line which supplies the signal to the tip of the needle or may employ the same coaxial feed line used in MWA itself.

Alternatively, the ablation needle 14 may comprise an integrated microwave source.

The antennae 16 of the antenna array 6 therefore all (or a subset of the antennae 16) act to receive the signal emitted by the ablation needle 14. Using the ablation needle 14 as the signal source avoids having to sequentially connect each of the antennae 16 to the transmit path and thus allows the scan time to be drastically reduced, potentially allowing real time operation.

Although the ablation needle 14 has been described as being automatically guided to the target, it may instead be manually guided, with its location being tracked inside the body part and displayed on a model of the body part along with the target's location so that it can be guided towards the target. A vector which extends from the end of the ablation needle may be projected onto the image to show the trajectory of the needle and to help the clinician guide the needle towards the target. The image may be repeatedly updated as the needle moves towards the target.

Although the shell 18 has been described as having a plurality of frustoconical apertures 32 for providing access to the breast, other arrangements may be used. In particular, the shell 18 may have a plurality of circumferential slots. The angular spacing of the slots corresponds to the available angular rotation of the antenna array 6. Each slot, under rotation, gives access to a volume of tissue which typically overlaps to some degree with adjacent slots in order to offer some options in needle placement.

Figure 6:
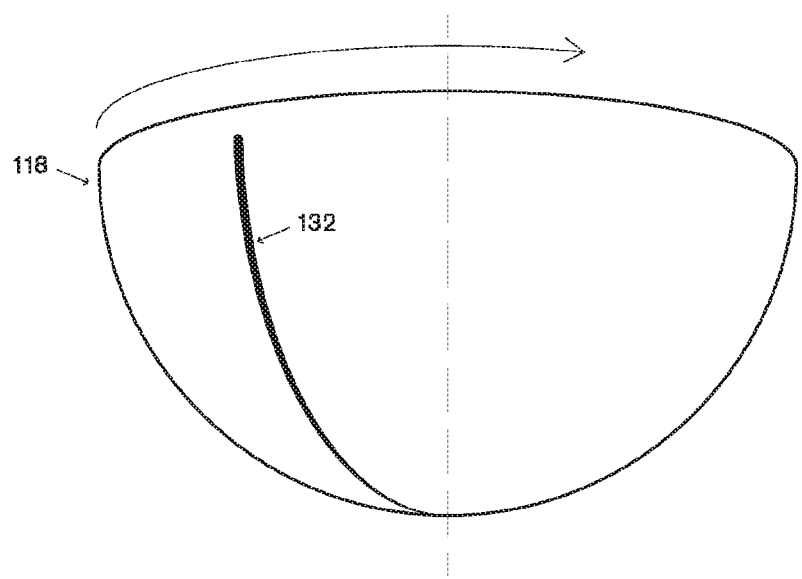
FIG. 6 is a perspective view of an alternative antenna shell used in the medical imaging system.

In particular, FIG. 6 shows an alternative embodiment of a shell 118 which may be used where the antenna array 6 is able to rotate through 180°. The shell 118 comprises a single slot 132 which passes through the axis of rotation from each side of the shell 118 (or two diametrically opposed slots with a discontinuity at the axis of rotation). The shell 118 is rotatable through 180° such that the slot 132 is able to allow the ablation needle 14 to access the entire breast 36.

Figure 7:
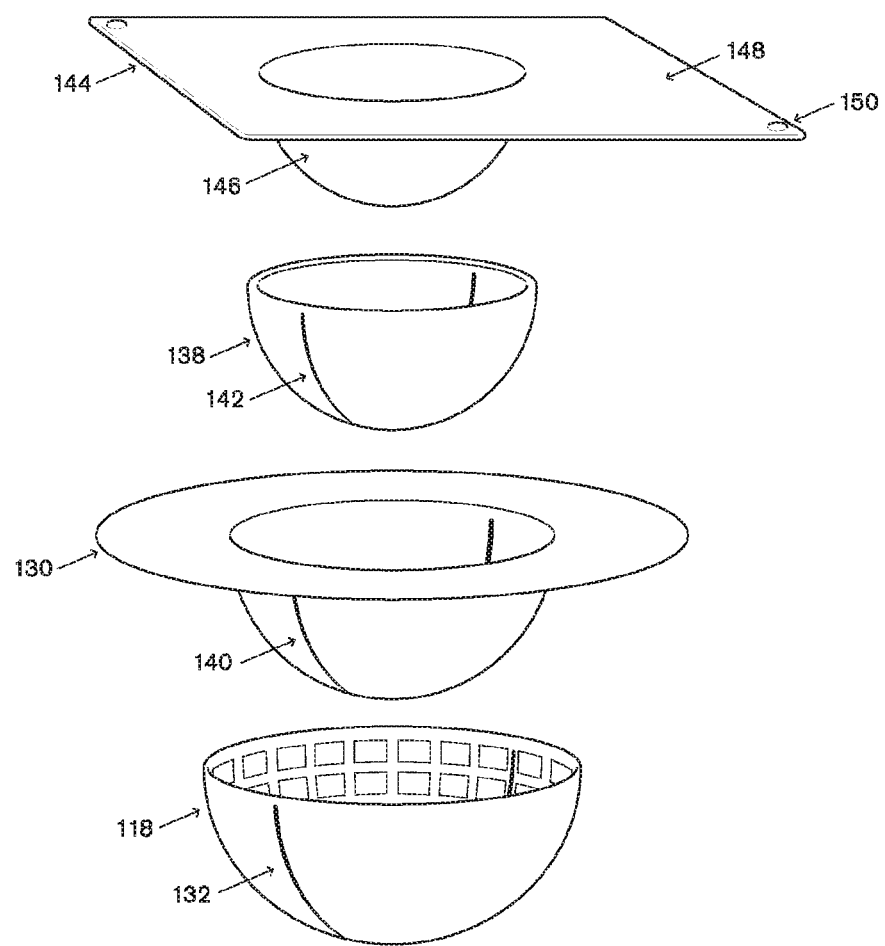
FIG. 7 is an exploded view of an assembly comprising the antenna shell of FIG. 6.

As shown in FIG. 7, the shell 118 is used with a cup 130 and, if required, an insert 138. The cup 130 has a complementary shape to the shell 118 such that if fits snugly within the shell 118 and, in turn, the insert 138 has a complementary shape to the cup 130 such that if fits snugly within the cup 130.

The cup 130 is provided with a slot 140 which corresponds to the slot 132 of the shell 118. Similarly, the insert 138 is provided with a slot 142 which corresponds to the slot 132 of the shell 118. The cup 130 and, if used, the insert 138 are disposed within the shell 118 such that the slots 132, 140, 142 of the shell 118, cup 130 and insert 138 are all aligned with one another. The slots 132, 140, 142 therefore provide access to the breast 36 from the exterior of the shell 118. The cup 130 and insert 138 are connected to the shell 118 so as to prevent relative rotation and thus to maintain the alignment of the slots 132, 140, 142. In particular, the cup and insert may be provided with locating tabs which prevent rotation relative to the shell 118.

As described with respect to the previous embodiment, a layer of coupling fluid may be inserted in the gap between the shell 118 and the cup 130 and also in the gap between the cup 130 and the insert 138. The slots 132, 140, 142 may be fitted with a gasket to prevent the escape of coupling fluid.

To allow the shell 118 to rotate relative to the breast 36, a disposable tray 144 is used. The tray 144 is made from a biocompatible polymer, such as PEEK, HIPS, PET. The tray comprises a central section 146 which is curved to conform to the underlying cup 130 or insert 138. In particular, the central section 146 may be part or hemi-spherical. Disposable trays may be provided in different sizes that correspond to the internal dimensions of each available insert (and cup) respectively so that a low-compliance fit to the underlying surface is achieved. A planar rim 148 extends from the central section 146. The material thickness over the central section 146 may be less than that of the planar rim 148. The planar rim 148 may therefore provide structural rigidity to the disposable tray 144, while the thin central section 146 ensures that the dielectric properties of the matching interface between the cup/inserts and patient is not disturbed.

The disposable tray 144 is held stationary against the breast 36 while the shell 118, cup 130 and insert 138 are rotated to properly align the slots 132, 140, 142 with the desired location over the breast 36 from which to perform the ablation procedure. The disposable tray 144 may be provided with location tabs 150 or the like which engage with complementary features on a stationary housing (not shown) of the antenna array 6. The disposable tray 144 is therefore fixed in position and prevented from rotating with the shell 118 and the intermediate component(s). The disposable tray 144 provides little resistance to the rotation of the shell 118 and so the patient does not feel the shell 118 being moved into position.

It will be appreciated that the disposable tray 144 lies over the aligned slots 132, 140, 142 and so obstructs the ablation needle 14. However, the material of the disposable tray 144 is suitably thin than it can be punctured by the needle. The ablation needle 14 punctures the tray 144 and breast tissue at a sufficiently high speed and force to minimize the breast tissue shrinking away from the surface of the tray 144. This therefore ensures that the ablation needle 14 is guided accurately to the target. Further, at least over the central section 146, the material of the disposable tray 144 may have low-shear characteristics such that when it is punctured by the ablation needle 14, the fracturing characteristic of the polymer can be controlled.

A drainage arrangement may be included to ensure that any coupling fluid that flows out of the slots in the array is channeled away from the main electro-mechanical components of the system.

The system described herein is capable of both providing a clinical breast microwave image showing a suspicious lesion and also locating and guiding an ablation needle to the lesion in order to perform an ablation procedure.

As the guidance of the ablation needle is performed by the same system which identifies the target, the patient may potentially remain in position throughout the procedure such that the breast retains registration throughout.

The system provides significant benefits over previously known systems and techniques. In particular, the system provides precise positioning of the ablation needle with respect to the acquired image, so that the clinician has a high degree of confidence that the proposed trajectory of the needle will intersect the target. This reduces the number of needle insertions/withdrawals and the risk of seeding malignant cells along multiple needle tracks.

As described previously, the target may be identified by performing a biopsy of a region of interest. The guidance of the biopsy may be achieved in a similar manner to that used for the ablation procedure. In fact, the ablation needle may be replaced by a biopsy needle during this procedure or a separate biopsy probe provided as part of the system.

Although the system has been described with reference to the imaging of a breast, it will be appreciated that it may be adapted for other areas of the body.

It will be appreciated that the processor 4 need not display, or indeed, generate, an image of the internal structure of the breast in order to identify a region of interest. The region of interest may instead be determined based on the raw data.

In other arrangements, the cup of the antenna array may be dispensed with or integrated into the shell in which the antennae are located.

The system may employ multiple transmit and receive paths, such that data can be recorded from multiple antennas simultaneously, and may even comprise a number of transmit and receive paths corresponding to the number of antennas, such that data can be recorded from all antennas simultaneously. In an alternative topology, the switching matrix could be removed thus allowing each antenna to be connected to a transmitting/receiving device.

Alternatively, more than one antenna may be operated at a time in a frequency multiplexed operation. Multiplexed operation may have significant advantages where high speed tracking of the needle is required.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

The invention is not limited to the embodiments described herein, and may be modified or adapted without departing from the scope of the present invention.

The invention claimed is:

1. A medical imaging system comprising:
  a microwave antenna array comprising a plurality of antennae, the plurality of antennae including a transmitting antenna and a plurality of receiving antennae, wherein the transmitting antenna is configured to transmit microwave signals so as to illuminate a body part of a patient and the receiving antennae are configured to receive the microwave signals following scattering within the body part;
  a processor configured to process the scattered microwave signals and generate an output indicative of the internal structure of the body part to identify a target within the body part; and
  an ablation probe comprising an ablation needle movable relative to the microwave antenna array;
  wherein the plurality of receiving antennae are embedded within a substrate, the substrate includes one or more openings extending through the substrate and disposed between the plurality of receiving antennae in the microwave antenna, the one or more openings configured to receive the ablation probe and position the ablation probe between the plurality of receiving antennae, and wherein the plurality of receiving antennae are further configured to receive microwave signals scattered or emitted by the ablation needle and the processor is further configured to monitor a position of the ablation needle as it is guided to the target within the body part.

2. A medical imaging system as claimed in claim 1, wherein the processor is further configured to guide the ablation needle to the target within the body part.

3. A medical imaging system as claimed in claim 1, wherein the one or more openings are conical.

4. A medical imaging system as claimed in claim 1, wherein the one or more openings are provided with sealing gaskets.

5. A medical imaging system as claimed in claim 1, wherein the one or more openings comprise one or more slots.

6. A medical imaging system as claimed in claim 1, wherein the substrate comprises a plurality of said one or more openings and wherein the processor is configured to select one of the plurality of one or more openings for introducing the ablation needle.

7. A medical imaging system as claimed in claim 1, wherein the ablation probe is mounted on an articulated arm configured to maneuver the ablation probe relative to the antenna array.

8. A medical imaging system as claimed in claim 7, wherein the articulated arm is a robotic arm.

9. A medical imaging system as claimed in claim 1, wherein the ablation needle is configured to emit microwave signals which are received by the plurality of receiving antennae.

10. A medical imaging system as claimed in claim 9, wherein the ablation needle comprises a coaxial feed line which transmits the microwave signals.

11. A medical imaging system as claimed in claim 1, wherein the ablation needle comprises a microwave marker at its tip.

12. A medical imaging system as claimed in claim 1, wherein the processor is configured to perform a first data acquisition and analysis operation when identifying the target and to perform a second data acquisition and analysis operation when guiding the ablation needle, the second data acquisition and analysis operation being faster than the first data acquisition and analysis operation.

13. A medical imaging system as claimed in claim 1, wherein the processor is further configured to monitor the target during an ablation procedure performed by the ablation probe.

14. A medical imaging system as claimed in claim 13, wherein the receiving antennae of the microwave antenna array receive a signal emitted by the ablation needle.

15. A medical imaging system as claimed in claim 13, wherein the processor is further configured to determine a temperature or temperature profile of the target based on permittivity and/or conductivity values measured from the scattered microwave signals during an ablation procedure.

16. A medical imaging method comprising:
   illuminating a body part of a patient with microwave signals emitted by a transmitting antenna of an microwave antenna array, wherein the microwave antenna array is formed on a substrate and wherein the substrate includes one or more openings configured to receive an ablation needle of an ablation probe to provide access to the body part;
   receiving the microwave signals following scattering within the body part at a plurality of receiving antennae of the microwave antenna array;
   processing the scattered microwave signals to generate an output indicative of the internal structure of the body part;
   identifying a target within the body part from the output;
   receiving the ablation needle through one of the one or more openings and between the plurality of receiving antennae in the microwave antenna array;
   guiding the ablation needle to the target within the body part by monitoring microwave signals scattered or emitted by the ablation needle using the receiving antennae; and
   performing an ablation procedure using the ablation probe in which a signal is emitted from the ablation needle so as to heat the target.

17. A method as claimed in claim 16 and further comprising:
   monitoring the target during the ablation procedure.

18. A method as claimed in claim 17, wherein monitoring the target comprises receiving at the receiving antennae of the microwave antenna array a signal emitted by the ablation needle during the ablation procedure.

19. A method as claimed in claim 17, wherein monitoring the target comprises determining permittivity and/or conductivity values for the target from the scattered microwave signals received during the ablation procedure; and determining a temperature or temperature profile of the target based on the measured permittivity and/or conductivity.

* * * * *